United States Patent [19]

Koskinen

[11] Patent Number: 5,589,689
[45] Date of Patent: Dec. 31, 1996

[54] INFRARED DETECTOR WITH FABRY-PEROT INTERFEROMETER

[75] Inventor: Yrjö Koskinen, Helsinki, Finland

[73] Assignee: Vaisala Oy, Helsinki, Finland

[21] Appl. No.: 499,188

[22] Filed: Jul. 7, 1995

[30] Foreign Application Priority Data

Jul. 7, 1994 [FI] Finland ................... 943251

[51] Int. Cl.⁶ .................................. G01J 5/10
[52] U.S. Cl. .................. 250/339.01; 250/338.1
[58] Field of Search ............. 250/339.01, 370.06, 250/338.4, 338.1; 257/432

[56] References Cited

U.S. PATENT DOCUMENTS

| | | | |
|---|---|---|---|
| 4,158,133 | 6/1979 | Spaeth et al. | 250/214 R |
| 4,902,136 | 2/1990 | Mueller et al. | 356/419 |
| 5,144,498 | 9/1992 | Vincent | 359/885 |
| 5,216,237 | 6/1993 | Ritchie et al. | 250/214.1 |
| 5,321,539 | 6/1994 | Hirabayashi et al. | 359/94 |
| 5,365,770 | 11/1994 | Meitzler et al. | 250/338.4 |

FOREIGN PATENT DOCUMENTS

| | | | |
|---|---|---|---|
| 253002 | 1/1988 | European Pat. Off. | 250/338.1 |
| 622857 | 11/1994 | European Pat. Off. | |
| 681047 | 12/1992 | Switzerland | |

OTHER PUBLICATIONS

K. Aratani et al., "Surface Micromachined Tuneable Interferometer Array", The 7th International Conference on Solid-State Sensors and Actuators, 1993. no month.
T. W. Kenney et al., "Electron Tunnel Sensors", J. Vac. Sci. Technol. A., vol. 10, No. 4, Jul./Aug. 1992.
S. Bauer et al., "Thin Metal Films As Absorbers for Infrared Sensors", Sensors and Actuators A, 37–38 (1993) pp. 497–501. no month.
R. Lenggenhager et al., "Improved Thermoelectric Infrared Sensor Using Double Poly CMOS Technology", The 7th International Conference on Solid–State Sensors and Actuators, 1993, p. 1008. no month.

*Primary Examiner*—Carolyn E. Fields

[57] ABSTRACT

The invention relates to a silicon micromechanically fabricated infrared detector having an infrared radiation absorbing layer (7, 44) deposited on an insulating substrate and a detector (11, 24, 25) for detecting the amount of radiation absorbed in the metallic absorbing layer. According to the invention, on the path of the radiation, prior to the absorbing layer (7, 44) is located an electrically controllable Fabry-Perot interferometer (1, 2, 5) manufactured by silicon micromechanical techniques and having the absorbing layer (7, 44) integrally coupled with one of the mirrors (1, 2) thereof.

20 Claims, 5 Drawing Sheets

INFRARED DETECTOR WITH FABRY-PEROT INTERFEROMETER

The invention is related to a silicon micromechanically fabricated infrared detector.

The invention is intended for applications in optical concentration measurements of gases, liquids or solid materials in the IR range.

BACKGROUND OF THE INVENTION

Gas concentration is conventionally measured by means of the absorption of infrared radiation. The measurement techniques are categorized into dispersive and nondispersive IR methods (NDIR, nondispersive infrared). The dispersive method is based on the use of a grating or a prism for measurements on multiple wavelengths. The nondispersive method employs a wider spectral range of the infrared range. Nondispersive infrared analyzers have a simpler construction which is easier to use. The wavelength range of measurement is conventionally selected by means of a bandpass filter.

A measurement system based on NDIR techniques usually comprises the following parts: an IR radiant source, a measurement channel, a bandpass filter and an IR detector. The method has generally been sufficiently selective with respect to the material being measured, while the instability of the analyzer equipment has posed a problem. Such instability is related to the aging of the IR radiant source, contamination of the measurement channel and sensitivity changes of the IR detector. To overcome such an instability problem, a measurement method has been used in which the measurement is performed at two different wavelength bands. One of the bands is selected to coincide with the absorption lines of the gas being measured while the other band (reference band) is set aside from the absorption band. Here, two separate bandpass filters are required. An alternative approach to the construction of the measurement apparatus is either to mount a pair of mechanically changeable filters in front of the IR detector, or alternatively, use two fixed filters combined with two separate IR detectors. The changing mechanism for the filter pair is usually implemented by means of a rotating disk.

The disadvantages of the above-described technique include a complicated construction of the mechanical structures of the measurement apparatus and, resultingly, a relatively high cost of the implementation of the measurement apparatus. The bandpass filter conventionally employed in the measurement apparatus is a special component carrying a rather high price. The rotating disk is hampered in use by its rather short life cycle due to the wear of its bearings. Furthermore, the contamination of the separate bandpass filters occurs at different rates causing an error in the measurement. The use of two separate fixed bandpass filters and IR detectors is hampered by the different aging rates of the IR detectors and the different contamination rates of the bandpass filters.

K. Aratani et al., "Surface Micromachined Tuneable Interferometer Array," The 7th International Conference on Solid-State Sensors and Actuators, Transducers '93, 678, Yokohama 1993, discloses an electrostatically tuneable Fabry-Perot interferometer component manufactured by surface micromechanical techniques. The component includes an integral photodiode acting as the light detector that has been implemented by processing a p-n junction into the silicon substrate. The components are fabricated into an interferometer array in which the size of each component is only 20×20 µm. The application of the array is to function as a light modulator in optical data transmission. Because a silicon diode is used in the component as the light detector, its use at wavelengths longer than approx. 1.1 µm is impossible, whereby the use of this component in concentration measurements is essentially limited. The application of the component is also restricted by its small area making the output signal of the light detector excessively weak for use as a component of an NDIR measurement apparatus.

T. W. Kenny et al., "Novel Infrared Detector Based on a Tunneling Displacement Transducer," J. Vac. Sci. Technol. A10(4) (1992), discloses a silicon micromechanically fabricated infrared detector operating on the principle of the so-called Golay cell in which the detection of infrared radiation is based on the measurement of thermal expansion of a gas in a sealed chamber. The infrared radiation is absorbed in the wall of the chamber formed by a thin membrane with an extremely low thermal mass. Resultingly, heat is transferred from the membrane to the gas in the sealed chamber, whereby the temperature increase of the gas tends to expand the gas thus causing a movement of the membrane. The displacement of the membrane is measured from the tunneling current between a thin, pointed electrode manufactured by silicon micromechanical techniques and the membrane. Such a component acts as a wideband optical IR detector, and its use in concentration measurements would require a separate bandpass filter.

S. Bauer et al., "Thin Metal Films as Absorbers for Infrared Sensors," Sensors and Actuators A, 37–38, (1993), pp. 497–501, discusses the use of thin metal foils as absorption materials of thermal IR detectors. A freely suspended thin metal film can maximally absorb 50% of the IR radiation impinging on it. However, significant improvement of absorption can be achieved by using a substrate material of suitable refractive index which is coated by a metallic film. Then, the magnitude of absorption becomes strongly dependent on the wavelength of the IR radiation. However, Bauer describes no method of limiting absorption to a given wavelength range. Therefore, also this embodiment requires the use of a separate bandpass filter in concentration measurements.

Micromechanical techniques have been widely applied to the manufacture of thermal IR detectors. Such techniques are based on thermally insulating the active, IR radiation absorbing part of the detector from the silicon substrate of the detector. The temperature change of the active part can be measured by means of a thermocouple integrated in the structure, a pyroelectric material, or a temperature-sensitive resistor. All structures known in the art employ wideband optical detectors.

SUMMARY OF THE INVENTION

It is an object of the present invention to overcome the drawbacks of the above-described techniques and to achieve an entirely novel type of selective infrared detector.

The goal of the invention is achieved by manufacturing the infrared detector integral with a bandpass filter. Additionally, the spectral range of the bandpass filter is made electrically tunable without using any moving elements subject to wear. The bandpass filter is implemented as a Fabry-Perot interferometer manufactured by means of surface micromechanical techniques. The function of the IR detector is based on the measurement of temperature rise caused by the absorption of IR radiation into the interferometer. IR radiation is absorbed in the detector structure only at the transmission band of the Fabry-Perot interferometer.

The invention offers significant benefits over conventional techniques. The Fabry-Perot interferometer and its integral thermal IR detector employed for concentration measurements are implemented using an entirely novel type of structure. In the embodiment according to the present invention, the FPI element and the thermal IR detector are incorporated in a single component manufactured by silicon micromechanical techniques.

Silicon micromechanical techniques make the component cost-effective in mass production. In an embodiment according to the prior art, the separate FPI and detector components have to be coupled with each other which is a complicated operation causing additional costs. The embodiment according to the present invention is capable of overcoming these disadvantages and eliminating the surplus costs.

The connection of a separate FPI component with a detector causes optical losses in the optimal focusing of the IR radiation transmitted through the FPI component onto the active surface of the detector. The embodiment according to the present invention eliminates such optical losses thus rendering an improved sensitivity of the IR detector.

BRIEF DESCRIPTION OF THE DRAWINGS

In the following, the invention will be examined in more detail by means of exemplifying embodiments with reference to the attached drawings, in which:

FIG. 1b is a top view of the Fabry-Perot interferometer shown in FIG. 1a;

FIG. 3b is a graph showing the spectral absorption curve of the structure shown in FIG. 3a;

DESCRIPTION OF THE PREFERRED EMBODIMENTS

Figure 1A:
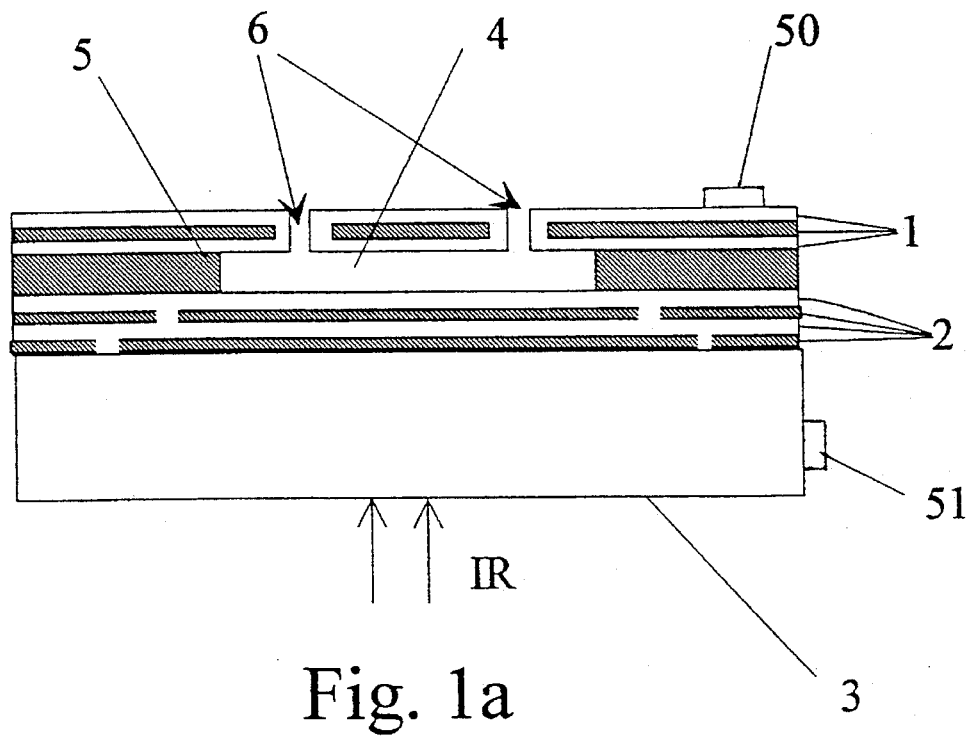
FIG. 1a is a longitudinally sectional side view of a Fabry-Perot interferometer having its mirrors implemented as a multilayer thin-film structure.
Figure 1B:
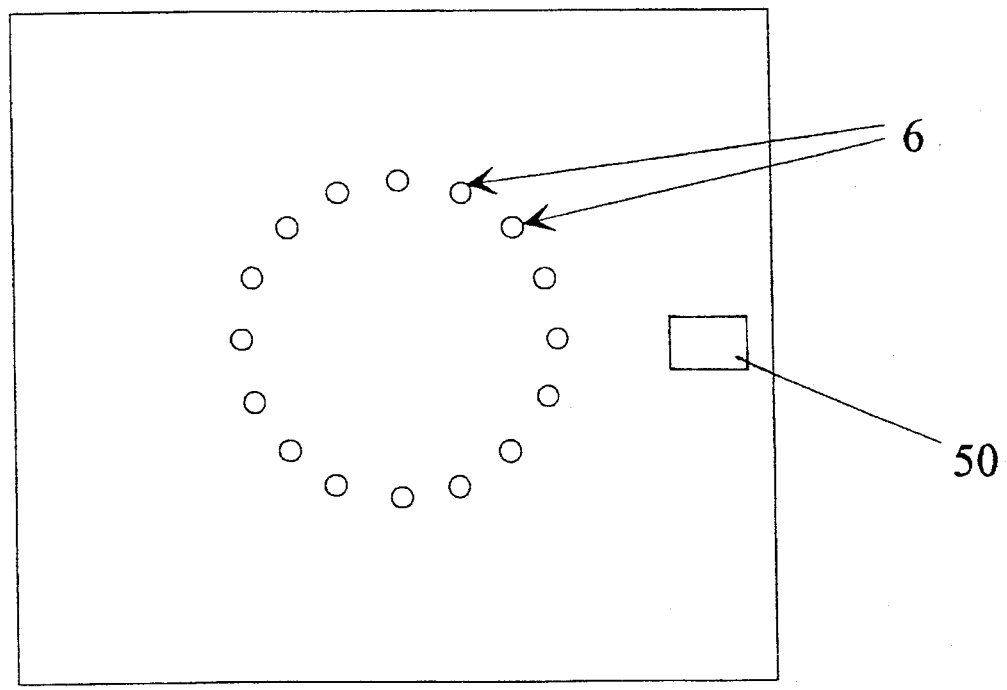

A Fabry-Perot interferometer (FPI) is formed by two opposedly parallel, semitransparent mirrors. Referring to FIGS. 1a and 1b, a possible structure is shown for an FPI manufactured by surface micromechanical methods. The upper mirror 1 and lower mirror 2 of the interferometer construction are fabricated into multilayer structures using thin-film techniques. The thin-film layers of the upper mirror are: polysilicon, silicon dioxide and polysilicon. The structure of the lower mirror 2 is otherwise similar except that one silicon dioxide layer is added. The thin-film layers of the mirrors can be grown by means of a CVD method onto a lightly doped silicon substrate 3 having good IR transmittance. An etalon 4 between the mirrors 1 and 2 is produced by etching away a sacrificing layer 5 via openings 6 made in the upper mirror. The sacrificing layer 5 may be of, e.g., silicon dioxide.

When the mirror 1 or 2 fabricated as a thin-film structure is desired to have maximum reflectance at a wavelength $\lambda$, the thickness of the thin-film layers must be equal to $\lambda/(4n)$ (where n is the refractive index of the material of the thin-film layer). The reflectance of the mirror is the higher the greater the differences of the refractive indices of the layers in the multilayer structure. A further requirement set on the materials of the thin-film structure is that their absorption at the desired wavelength passband of the FPI be as low as possible. Suitable materials are, e.g., lightly doped polysilicon, silicon dioxide and silicon nitride.

Figure 2:
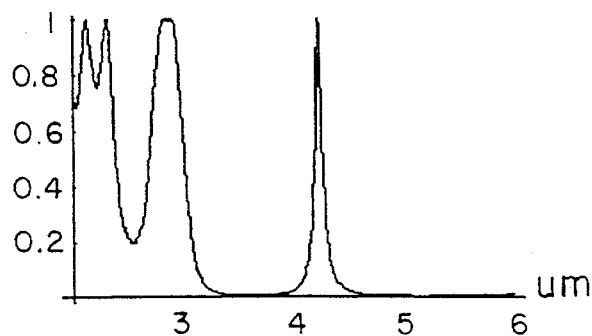
FIG. 2 is a graph showing the spectral transmittance curves of the structure shown in FIGS. 1a and 1b.

The determination of the spectral transmittance of an FPI implemented by means of thin-film multilayer structures is described in H. A. McLeod, "Thin Film Optical Fibers," Adam Hilger, Bristol (1986). The transmittance of the entire interferometer structure can be determined from the coefficients of reflection and transmission of the different interfaces of the thin-film layers in the structure. FIG. 2 shows the spectral transmittance curve for the structure illustrated in FIGS. 1a and 1b.

The positions of the passband wavelengths of an ideal FPI can be approximately calculated by means of the formula:

$$2d/m=\lambda \qquad (1)$$

where d is the etalon length between the mirrors, m is an integer (i.e., the fringe order of the FPI). In Eq. 1, the etalon medium between the mirrors is assumed to be air. In the structure shown in FIG. 1a, d=2.1 μm, and the passband corresponding to fringe order m=1 is approximately at 4.2 μm. At shorter wavelengths the passbands do not fall at the wavelengths given by Eq. 1, because the thicknesses of the mirrors in the FPI are dimensioned for maximum reflectance at approx. 4 μm. Resultingly, the reflectance properties are compromised at shorter wavelengths.

As the material of one of the layers in the mirrors illustrated in FIG. 1a is conductive polysilicon, a control voltage can be applied between mirrors via contact areas 50 and 51. Thus, an electrostatic force of attraction can be established between the mirrors that tends to deflect the upper mirror 1 closer to the lower mirror 2. The upper mirror is deflected over the portion where the sacrificing layer has been removed by etching. The area of the upper mirror bounded by the etch-through openings 6 remains sufficiently planar when the distance between the mirrors is altered by means of the electrostatic force. The planar area of the upper mirror may be termed the optically active area of the mirror. By means of a voltage applied between the mirrors 1 and 2, the distance between the optically active area and the lower mirror 2 can be controlled, and resultingly, as given by Eq. 1, the passband wavelength of the FPI. The diagonal dimension of the optically active area of the mirror may be varied in the range 0.2–2 mm.

When a Fabry-Perot interferometer is used in an NDIR measurement apparatus, at least one of the passbands related to a fringe order m is selected for use and the other passbands are blocked by means of suitable cutoff filters of shorter and longer wavelengths. The cutoff filter of shorter and longer wavelengths may be made from a suitable absorbing material having advantageous transmittance properties at the desired IR passband. The FPI can be utilized by way of altering the passband of the FPI with the help of the control voltage, thus performing the measurement at a number of wavelength bands.

Figure 3A:
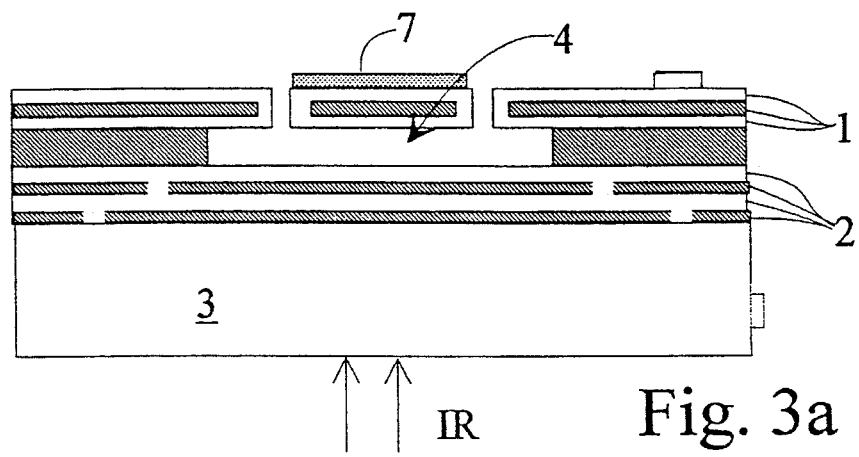
FIG. 3a is a longitudinally sectional side view of an IR radiation absorbing layer according to the invention integrated with a Fabry-Perot interferometer.

Referring to FIG. 3a, a structure according to the invention is shown having a Fabry-Perot interferometer serving as a filter fabricated integral with an absorbing layer 7. This structure is identical to that shown in FIG. 1a except for the metallic thin-film layer 7 performing as a partial absorber of IR radiation at wavelengths corresponding to the passband of the FPI. Such a thin metallic layer 7 functioning as the absorbing material can be fabricated onto the optically active area of the upper mirror 1 by, e.g., vacuum evaporation.

As absorption of IR radiation in the metallic layer 7 is due to free charge carriers, the absorption properties of the layer may be determined from the conductivity of the metallic layer 7. The above cited reference to Bauer gives the following equations from which the coefficient of reflection r and the coefficient of transmission t can be determined in the interface between two dielectric layers when a metallic thin-film layer is deposited between the layers:

$$r = (N_2 - N_1 + y)/(N_2 + N_1 + y) \quad (2)$$

$$t = 2 N_1/(N_2 + N_1 + y) \quad (3)$$

where $y = 377 \, \Omega/R_\square$, $R_\square$ is the sheet resistance of the metallic layer 7, $N_1$ and $N_2$ are the complex refractive coefficients of the dielectric materials. Subindex 1 denotes the material wherefrom the IR radiation impinges on the interface between the materials and subindex 2 denotes the material into which the radiation is transmitted. In the structure of FIG. 3a, $N_2 = 1$ (that is, the refractive coefficient or air).

Figure 3B:
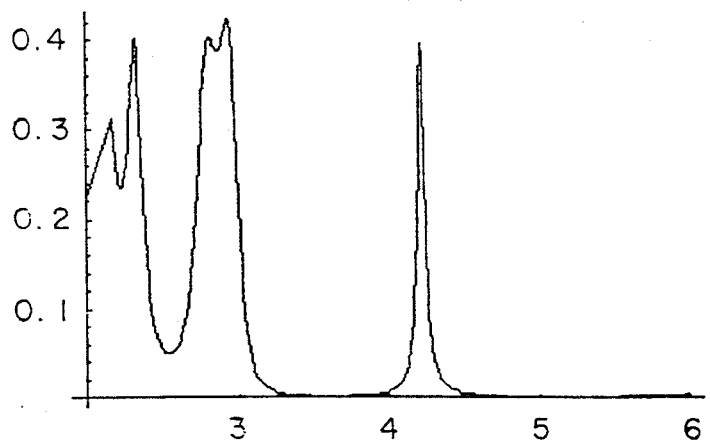

Shown in FIG. 3b is the spectral absorption curve computed on the basis of Eqs. 2 and 3 for an FPI where $R_\square = 160 \, \Omega$. It can be seen from FIGS. 2 and 3b that the absorption band of an FPI incorporating a metallic layer coincides with the absorption band wavelength of an FPI fabricated without the metallic layer. When the material of the mirror layer is, e.g., lightly doped or undoped polysilicon, silicon dioxide or silicon nitride, the absorption of such materials is insignificant over the wavelength range 1–8 μm as compared with the absorption caused by the metallic layer. The position of the absorption band in the diagram of FIG. 3b may be varied electrostatically by modulating the voltage applied between the mirrors.

The metallic layer used in the structure may be of gold, for instance. Then, a layer with a sheet resistance of 160 Ω may be as thin as approx. 20 nm.

Instead of metal, the material of the absorbing layer may be a semiconductor like polysilicon, for instance.

The embodiment according to the invention is capable of detecting the intensity of IR radiation absorbed in the FPI. The absorbed IR radiation elevates the temperature of the thermally insulated mirror, and such a temperature rise is converted with the help of the thermal detector into an electrical output voltage of the transducer. The transducer output voltage is proportional to the intensity of the impinging IR radiation over the absorption band of the FPI. The embodiment according to the invention is entirely novel in the sense that the component manufactured using silicon micromechanical techniques serves as both an interferometer and a thermal IR detector.

To achieve a high-efficiency detector, the mirror or mirrors of the FPI must have minimum thermal mass in order to produce maximum rise of mirror temperature at a given intensity of absorbed IR radiation. The detection of temperature change can be implemented with the help of thermocouples, a pyroelectric material, a temperature-sensitive resistor or a Golay-cell-type sensor integrated with the detector structure.

The thermal insulation of the upper mirror can be further improved by hermetically encapsulating the detector under such a high vacuum that the thermal conductivity of the gaseous medium filled etalon 4 is sufficiently reduced.

Referring to FIG. 3a, the structure illustrated therein has the absorbing mirror 1 thermally insulated from the substrate 3 by means of a thin, gas-filled cavity 4 between the mirrors 1 and 2. The cavity 4 serves as a good thermal insulator even if its thickness is only in the order of a few micrometers. When the absorbing mirror 1 is sufficiently thin, thermal conduction along the mirror to the supporting substrate 3 becomes an insignificant factor in thermal loss.

Figure 4:
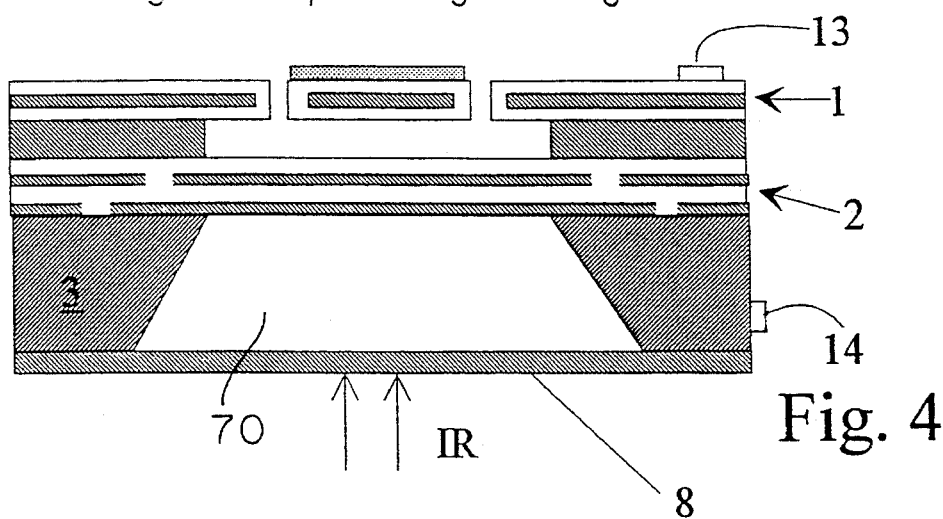
FIG. 4 is a longitudinally sectional side view of an alternative embodiment of an IR detector according to the invention equipped with a Fabry-Perot interferometer.

Referring to FIG. 4, an alternative structure is shown having a low thermal mass in both mirrors 1 and 2. Such a structure can be achieved by combined use of bulk and surface micromechanical techniques. The bulk 70 of silicon substrate 3 located below the lower mirror 2 is removed over the active detector area by means of anisotropic etching. As the mirrors 1 and 2 are located very close to each other and have a very low thermal mass, the temperature of the lower mirror 2 follows the temperature of the upper mirror. The structure illustrated in FIG. 4 achieves a greater temperature change than the structure shown in FIG. 3a, because heat conduction from the mirrors to the substrate 8 is insignificant when the thickness of the silicon substrate 3 is in the order of 0.5 mm.

Figure 5:
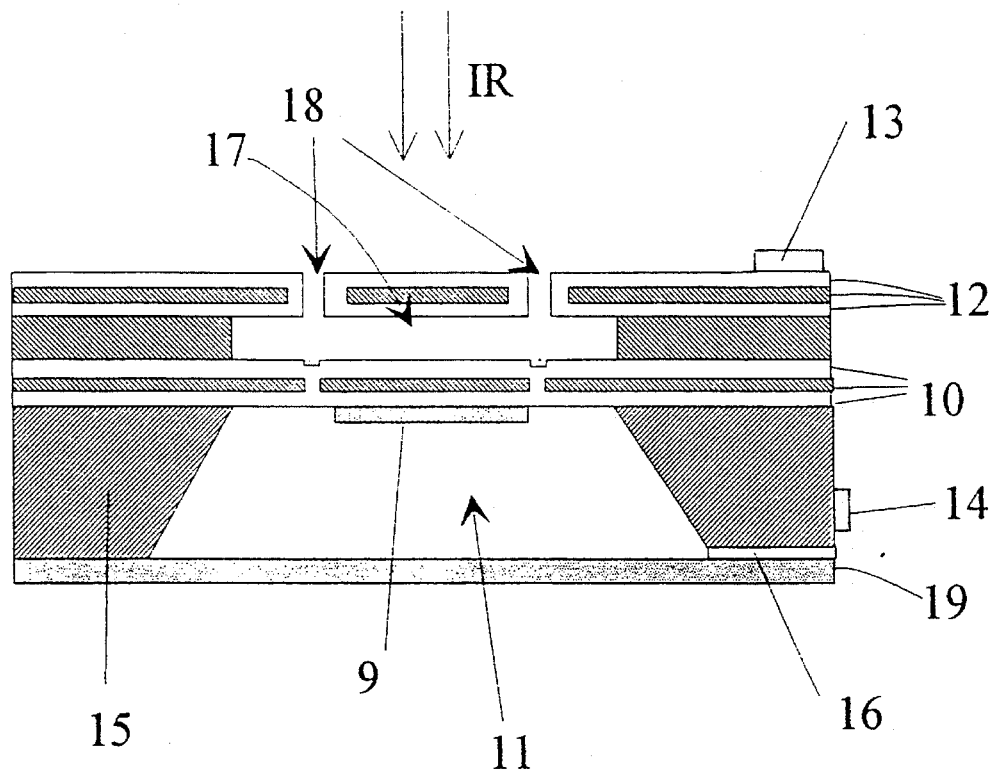
FIG. 5 is a longitudinally sectional side view of another alternative embodiment of an IR detector according to the invention equipped with a Fabry-Perot interferometer.

Referring to FIG. 5, an FPI is illustrated having a pneumatic IR detector integrated thereto. The function of the cell is such that IR radiation is first absorbed into a metallic layer 9 which then heats up the lower mirror 10. From the lower mirror 10 heat is transferred to the gas contained in the sealed chamber 11. When heating, the gas in the chamber 11 tends to expand imposing a pressure on the lower mirror 10 that causes a deflection of the lower mirror 10. The deflection is detected as a capacitance change between the lower mirror 10 and the upper mirror 12 when the pressure imposed on the lower mirror 10 results in a change of the distance between the lower mirror 10 and the upper mirror 12.

In addition to their optical function, the upper mirror 12 and the lower mirror 10 serve in the structure as the electrodes of the measurement capacitor, and a change in the capacitance between these electrodes is caused by the pressure change in the sealed chamber 11. One of the materials used in the upper and lower mirrors is appropriately doped silicon to make the electrodes suitably conducting for such a capacitance measurement. Electrical contact to the mirrors 10 and 12 is made via metallic contact pads 13 and 14.

In an NDIR measurement apparatus, the pneumatic IR detector is subjected to IR radiation chopped at a certain rate which generates pressure variations, that is, a sound in the chamber 11 at the same frequency with the radiation chopping rate. In the structure the sound is detected in the same fashion as in a capacitor microphone, whereby in the present structure the mirrors of the FPI serve as the electrodes of the microphone. Pressure variations are converted by conventional electronic techniques employed in capacitor microphones into an output voltage which is proportional to the intensity of the IR radiation imposed on the pneumatic IR detector at the absorption band of the FPI.

Referring again to FIG. 5, the structure shown therein has the sealed chamber 11 fabricated by etching away the volume of the silicon substrate 15 located below the lower mirror 10 by means of an anisotropic etch and by then pasting the silicon substrate 15 onto an underlayer 19. Between the underlayer 19 and the silicon substrate 15 is processed a thin groove 16 through which slow pressure variations in the ambient pressure are also transmitted to the chamber 11 thus equalizing pressure differences between the ambient pressure and the chamber 11. The groove is made so narrow that it cannot leak out the sound generated by the IR radiation in the chamber 11. The metallic layer 9 is produced by vacuum evaporation prior to the pasting of the substrate onto the underlayer 19. The upper mirror 12 is provided with etch-through openings 18 at such a close spacing that the gas can freely flow between the cavity 17 outdistancing the mirrors and the ambient gas space. Resultingly, the movement of the lower mirror 10 is advantageously prevented from causing compression or expansion of the gas contained between the mirrors 10 and 12 which would induce a force resisting the movement of the lower mirror 10. The detectivity of IR radiation can be improved by increasing the area of the mirror. The width of the optically active area of the mirror may be, e.g., 0.5–1 mm.

Figure 6:
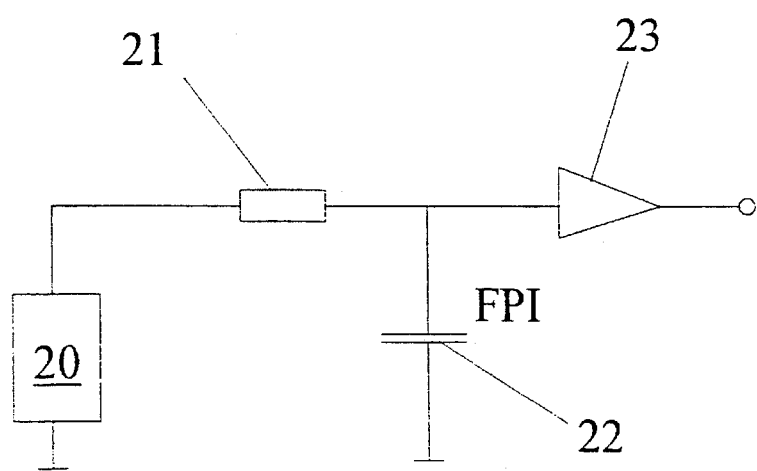
FIG. 6 is a circuit diagram suited for controlling the detector illustrated in FIG. 6.

Referring to FIG. 6, a circuit diagram is shown for the electronic control of the combination FPI-pneumatic IR detector when the FPI is receiving modulated IR radiation. A voltage supply 20 is arranged to provide a polarization voltage between the mirrors of the FPI. The voltage is taken via a resistor 21 of high resistance to the electrodes of the FPI, whereby the charge of the mirror electrodes remains essentially constant when the chopped IR radiation causes a capacitance change between the electrodes in the FPI. The voltage signal is amplified by means of a preamplifier 23. The polarization voltage applied between the mirrors produces a force of attraction between them and is thus capable of altering the distance between the mirrors. By adjusting the output voltage level of the voltage supply 20, the mutual distance between the mirrors is controlled so as to tune the absorption band of the interferometer to a desired wavelength.

The FPI must have a design such that mutual distance between the mirrors is distinctly greater in the unpolarized rest state than the mutual distance between the mirrors required for tuning to the wavelength used in the concentration measurement, whereby the latter operating distance is set through reducing the mutual distance between the mirrors by applying the polarization voltage. The higher the polarization voltage the larger the output voltage swing obtained from the pneumatic IR detector.

By using an electrically controlled voltage supply 20, concentration measurements can be performed at a number of different wavelength bands.

As the structure illustrated in FIG. 5 must be understood as an example only, it is obvious for a person versed in the art that the multilayer mirrors 10 and 12 of the FPI can be implemented in a variety of different ways. For instance, the structure shown in FIG. 5 may also be modified so that the metallic layer 9 is placed above the upper mirror 12, whereby the upper mirror 12 serves as the IR radiation absorbing element. Then, the IR radiation must be made to impinge on the mirrors from below through the hermetic chamber 11 and the transparent underlayer 19.

A characterizing property of the present invention is that the thermally insulated mirror of the FPI serving as the IR radiation absorbing element is adapted to communicate with the hermetic chamber in which the contained gas is heated by the absorption of IR radiation in the mirror. In the above-described embodiment according to the invention, the mirrors of the FPI also form a microphone serving for the detection of pressure variations in the hermetic chamber. Alternatively, detection can be carried out by fabricating a separate pressure transducer with silicon micromechanical techniques that communicates with the hermetic chamber.

Figure 7:
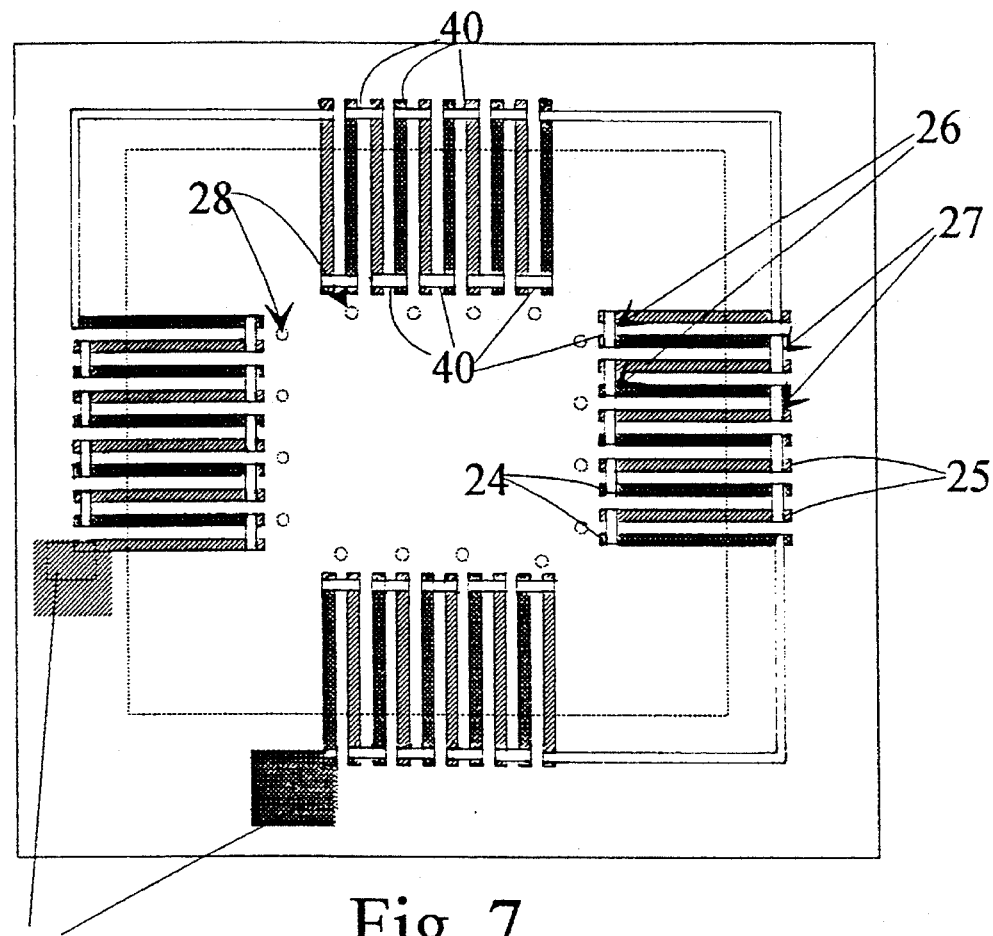
FIG. 7 is a top view of a third alternative embodiment of an IR detector according to the invention.
Figure 8:
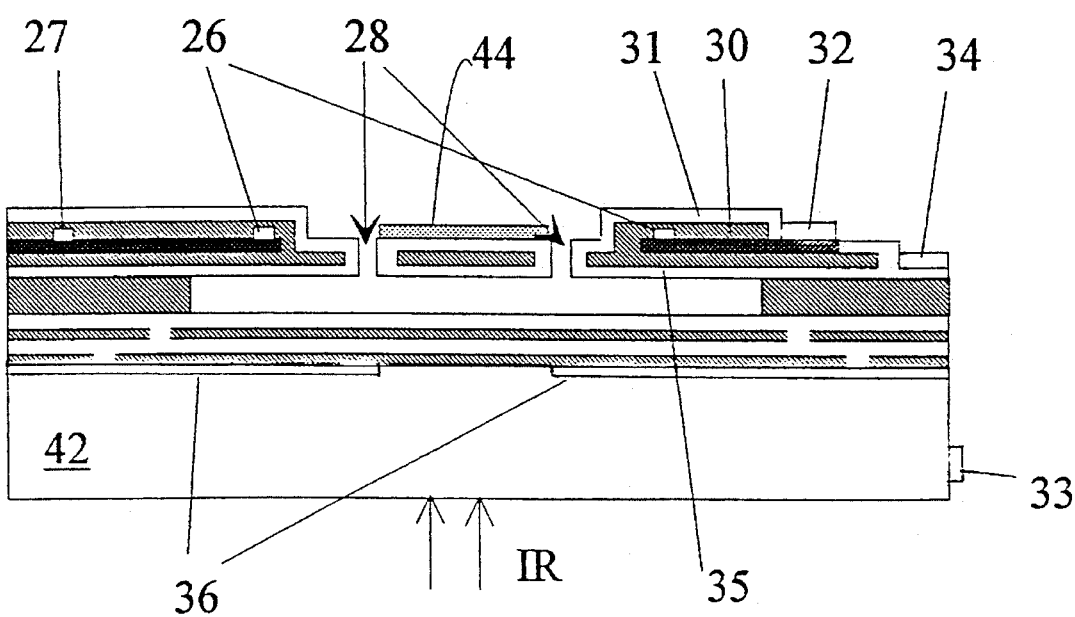
FIG. 8 is a longitudinally sectional side view of the IR detector illustrated in FIG. 7.

Referring to FIGS. 7 and 8, the function of a thermopile detector illustrated therein is based on a number of thermocouples connected in series. The thermocouple conductors are mutually connected to each other so as to form junctions in the "hot" area 26 and the "cold" area 27 of the detector, and the output voltage of each thermocouple is proportional to the temperature difference between the junctions. To achieve a higher output voltage, the thermopile detector utilizes a number of thermocouples connected in series.

The fabrication of a thermopile IR detector by silicon micromechanical techniques is well known in the art. Suitable materials for the thermocouples are, e.g., doped polysilicon and aluminium. R. Lenggenhager, H. Baltes, "Improved Thermoelectric Infrared Sensor Using Double Poly CMOS Technology," The 7th International Conference on Solid-State Sensors and Actuators, Transducers '93, Yokohama 1993, p. 1006, discloses a thermopile IR detector having the pn polysilicon thermocouples integrated in a thermally insulated multilayer thin-film structure.

Referring again to FIGS. 7 and 8, the Fabry-Perot interferometer illustrated therein has a thermocouple set integrated in the polysilicon layer of the upper mirror. FIG. 7 shows the FPI in a top view prior to the deposition of the protective layers onto the thermocouples. FIG. 8 shows a longitudinally sectional view of the completed structure. To the polysilicon layer is doped a p type conductor 24 and an n type conductor 25. The conductors are isolated from each other by etching away the polysilicon from between the conductors. The p and n type polysilicon conductors 24 and 25 are connected to each other by means of vacuum-evaporated aluminium strips 40. The junctions are located in the hot area 26 and the cold area 27 of the detector.

As shown in FIG. 8, the thermocouples are covered by depositing layers of silicon dioxide 30 and polysilicon 31 onto them that protect the structure during the etching-away of the sacrificing layer. The etching-away is performed by first processing etching openings 28 through the polysilicon layer. Finally, openings for the contact areas 32 of the thermocouples are etched in the protective layer deposited onto the structure shown in FIG. 8.

The control voltage of the FPI is taken via the contact areas 33 and 34. The first polysilicon layer 35 of the upper mirror is doped sufficiently conducting to assure a reliable ohmic contact. In this structure the polysilicon between the thermocouple contact area 32 and upper mirror contact area 34 must be undoped to assure sufficient electrical isolation between these contact areas.

Prior to the growth of the lower mirror, a metallic aperture 36 must be processed onto the silicon substrate 42 which is transparent to IR radiation only at the optically active area of the FPI. The aperture 36 allows IR radiation to be incident on metallic absorbing layer 44. Then, no IR radiation will impinge on the upper mirror at the thermocouples 24 and 25. Otherwise, the heavily doped polysilicon employed in the thermocouples and the metallic strips 40 might absorb IR radiation at unwanted wavelengths and thus change the absorption bandwidth of the FPI. This disadvantage is eliminated by means of the metallic aperture 36.

The thermal properties of the structure may be improved by thinning the silicon substrate as shown in FIG. 4. If the design requires the use of a metallic aperture as in the structure illustrated in FIG. 8, it may be implemented by a separate metal aperture.

The output voltage from the structure is obtained via contact areas 32. The output voltage is linearly proportional to the intensity of absorbed IR radiation. The voltage signal must be amplified by means of a low-noise preamplifier prior to taking it to the signal processing electronics employed for determining the concentration to be measured.

The structure illustrated in FIGS. 7 and 8 must be understood to represent an exemplary embodiment. To a person versed in the art it is obvious that a variety of different ways of implementing the thermocouples and the multilayer mirrors are available. The invention is characterized in that the thermocouples are integrated to one of the thermally insulated multilayer mirrors of the FPI.

The temperature rise of the FPI mirror may also be detected by means of a temperature-sensitive resistor. The material of the resistor may be lightly doped polysilicon, whereby its integration in the structure is easy as one of the materials already used in the mirrors of the FPI is polysilicon.

Figure 9:
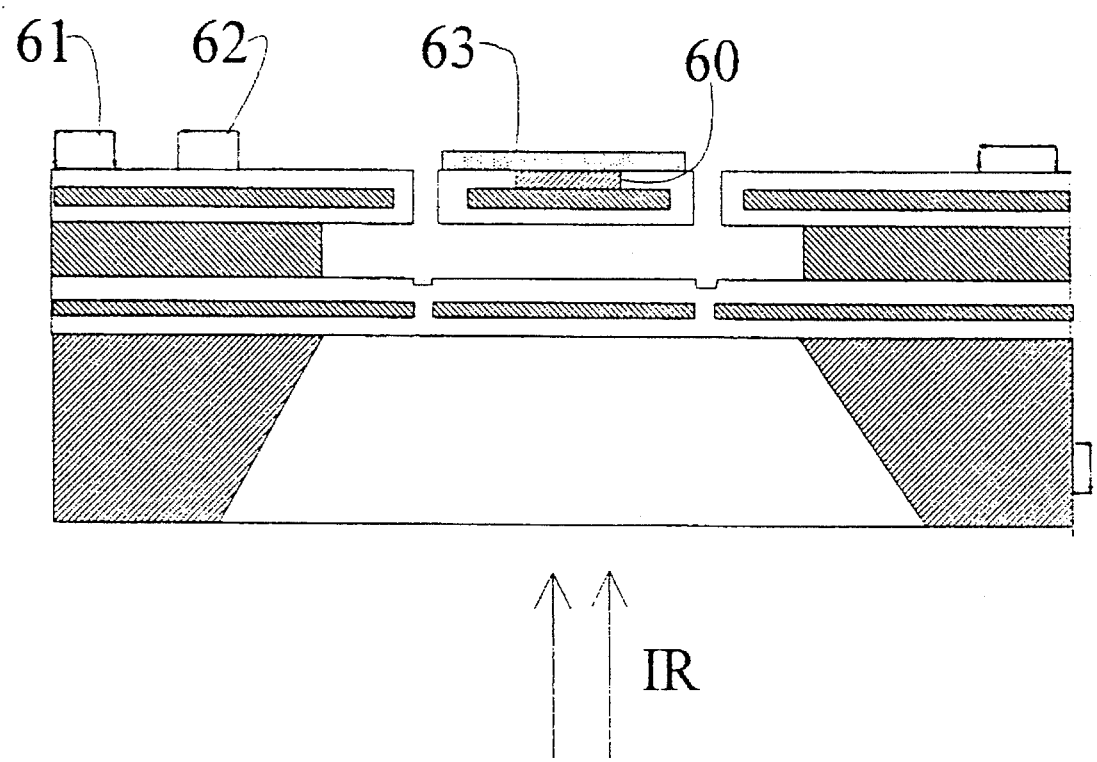
FIG. 9 is a side view of another alternative embodiment of an IR detector according to the invention.

FIG. 9 illustrates a bolometer-IR-detector 63 provided with a lightly doped portion 60 of the upper mirror as the temperature-sensitive resistor. A change in the resistance of the resistor is proportional to the intensity of the IR radiation absorbed by the bolometer. The value of the resistance 60 can be measured via contacts 61 and 62. Leads have been provided from the contacts to the ends of the resistor 60 by suitably doping the polysilicon of the upper mirror. The undoped area between the leads constitutes a sufficient insulator.

I claim:

1. A silicon micromechanically fabricated infrared detector comprising:

an electrically tuneable Fabry-Perot interferometer having mirrors and being manufactured by silicon micromechanical techniques;

an infrared radiation absorbing layer integrally coupled with one of the mirrors;

thermal detector means for detecting the amount of radiation absorbed into said absorbing layer.

2. An infrared detector as defined in claim 1, wherein the mirrors of the Fabry-Perot interferometer are spaced apart and form electrodes of a pressure transducer.

3. An infrared detector as defined in claim 2, wherein said absorbing layer heats up as it absorbs the infrared radiation thereby causing deflection of the one mirror; and further wherein the deflection is detected by the pressure transducer.

4. An infrared detector as defined in claim 3, wherein a deflection of another of the mirrors is controlled by electrical tuning of the electrically tuneable Fabry-Perot interferometer.

5. An infrared detector as defined in claim 3, further comprising:

a sealed chamber containing a gas, the gas being in thermal contact with said absorbing layer thereby heating up as said absorbing layer heats up;

wherein a pressure of the gas increases due to the heating up and causes the deflection of the one mirror.

6. An infrared detector as defined in claim 5, wherein the gas is in physical contact with the one mirror.

7. An infrared detector as defined in claim 5, further comprising:

a second substrate onto which the mirrors are mounted, the sealed chamber being formed in said second substrate.

8. An infrared detector as defined in claim 1, wherein said thermal detector means includes a thermocouple detector attached to the Fabry-Perot interferometer for detecting the radiation impinging on said absorbing layer.

9. An infrared detector as defined in claim 1, wherein said thermal detector means includes a temperature-sensitive resistor in the Fabry-Perot interferometer for detecting the radiation impinging on the absorbing layer.

10. An infrared detector as defined in claim 9, wherein said temperature-sensitive resistor is formed in the one mirror.

11. An infrared detector as defined in claim 1, further comprising: a second substrate onto which the mirrors are mounted, the mirrors including a lower mirror and an upper mirror, the lower mirror being located closer to the second substrate than the upper mirror, wherein the absorbing layer is located in the upper mirror.

12. An infrared detector as defined in claim 1, further comprising: a second substrate onto which the mirrors are mounted, the mirrors including a lower mirror and an upper mirror, the lower mirror being located closer to the second substrate than the upper mirror, wherein the absorbing layer is located in the lower mirror.

13. An infrared detector as defined in claim 1, wherein the mirror to which the absorbing layer is coupled has a low thermal mass.

14. An infrared detector as defined in claim 1, wherein the absorbing layer is made of polysilicon.

15. An infrared detector as defined in claim 1, wherein the absorbing layer is made of metal.

16. An infrared detector as defined in claim 1, wherein said thermal detector means is arranged in an area of the Fabry-Perot interferometer onto which the infrared radiation is not incident.

17. An infrared detector as defined in claim 1, wherein said thermal detector means includes n-type and p-type conductors arranged in series on a mirror of the Fabry-Perot interferometer.

18. An infrared detector as defined in claim 17, wherein said conductors are connected to each other at first connection locations and second connection locations, the first connection locations being heated to a higher temperature relative to the second connection locations.

19. An infrared detector as defined in claim 18, further comprising:

a displaceable portion of the one mirror, said portion being displaceable by electrically tuning the Fabry-Perot interferometer, said conductors being attached to the one mirror and substantially surrounding said portion, wherein the first connection locations are closer to a center of said portion than the second connection locations.

20. An infrared detector as defined in claim 1, wherein said thermal detector means detects the amount of heat generated by radiation being absorbed into said absorbing layer, the detected amount of heat corresponding to the amount of radiation absorbed.

* * * * *